(12) United States Patent
Shan et al.

(10) Patent No.: US 6,930,217 B2
(45) Date of Patent: *Aug. 16, 2005

(54) CATALYST CONTAINING MICROPOROUS ZEOLITE IN MESOPOROUS SUPPORT AND METHOD FOR MAKING SAME

(75) Inventors: Zhiping Shan, Delft (NL); Jacobus Cornelius Jansen, Delft (NL); Chuen Y. Yeh, Edison, NJ (US); Johannes Hendrik Koegler, Heidelberg (DE); Thomas Maschmeyer, Delft (NL)

(73) Assignee: ABB Lummus Global Inc., Bloomfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/875,087

(22) Filed: Jun. 24, 2004

(65) Prior Publication Data

US 2005/0013773 A1 Jan. 20, 2005

Related U.S. Application Data

(60) Division of application No. 09/995,227, filed on Nov. 27, 2001, now Pat. No. 6,762,143, which is a continuation-in-part of application No. 09/390,276, filed on Sep. 7, 1999, now Pat. No. 6,358,486.

(51) Int. Cl.[7] .............................. C07C 2/66; C07C 5/22; C07C 2/58; C10G 11/00; C10G 73/02
(52) U.S. Cl. ........................ 585/467; 585/722; 585/739; 585/666; 585/481; 208/28; 208/120.01
(58) Field of Search .................................. 585/467, 722, 585/739, 666, 481; 208/28, 120.01

(56) References Cited

U.S. PATENT DOCUMENTS

| | | |
|---|---|---|
| 5,057,296 A | 10/1991 | Beck |
| 5,098,684 A | 3/1992 | Kresge et al. |
| 5,108,725 A | 4/1992 | Beck et al. |
| 5,110,572 A | 5/1992 | Calabro et al. |
| 5,191,134 A | 3/1993 | Le |
| 5,191,148 A | 3/1993 | Degnan et al. |
| 5,264,203 A | 11/1993 | Beck et al. |
| 5,800,800 A | 9/1998 | Pinnavaia et al. |
| 6,133,186 A | 10/2000 | Gosselink et al. |
| 6,346,140 B2 | 2/2002 | Miyazawa et al. |

FOREIGN PATENT DOCUMENTS

| | | |
|---|---|---|
| EP | 0847802 | 6/1998 |
| WO | WO 97/20016 | 6/1997 |
| WO | WO 01/17901 | 3/2001 |

*Primary Examiner*—Thuan D Dang
(74) *Attorney, Agent, or Firm*—Dilworth & Barrese, LLP

(57) ABSTRACT

A catalytic material includes a microporous zeolite supported on a mesoporous inorganic oxide support. The microporous zeolite can include zeolite beta, zeolite Y or ZSM-5. The mesoporous inorganic oxide can be, e.g., silica or alumina, and can optionally include other metals. Methods for making and using the catalytic material are described herein.

6 Claims, 5 Drawing Sheets

CATALYST CONTAINING MICROPOROUS ZEOLITE IN MESOPOROUS SUPPORT AND METHOD FOR MAKING SAME

CROSS-REFERENCE TO RELATED APPLICATIONS

The present application is a divisional of U.S. application Ser. No. 09/995,227 filed Nov. 27, 2001 now U.S. Pat. No. 6,762,143, which is a continuation-in-part of U.S. application Ser. No. 09/390,276 filed Sep. 7, 1999 now U.S. Pat. No. 6,358,486 to which priority is claimed, and which is herein incorporated by reference.

BACKGROUND

1. Field of the Invention

The present disclosure is related to catalyst material containing zeolite embedded in a catalyst support, and particularly to a microporous zeolite embedded in a mesoporous support.

2. Background of the Art

Most of today's hydrocarbon processing technologies is based on zeolite catalysts. Zeolite catalysts are well known in the art and possess well-arranged pore systems with uniform pore sizes. However, these materials tend to possess either only micropores or only mesopores. Micropores are defined as pores having a diameter of less than about 2 nm. Mesopores are defined as pores having a diameter ranging from about 2 nm to about 50 nm.

Because such hydrocarbon processing reactions are mass-transfer limited, a catalyst with ideal pore size will facilitate transport of the reactants to active catalyst sites and transport of the products out of the catalyst.

SUMMARY OF THE INVENTION

A material useful in catalytic processing of hydrocarbons is provided herein. The material comprises a zeolite, and a porous inorganic oxide which includes at least 97 volume percent mesopores based on the micropores and mesopores of the inorganic oxide. The zeolite is preferably a microporous zeolite such as for example, zeolite beta, zeolite Y, or ZSM-5. A method for making and method for using the material are described herein.

The catalytic material described herein advantageously facilitates the transport of reactants to active catalyst sites and is about 5 times more active than the zeolite used alone.

BRIEF DESCRIPTION OF THE DRAWINGS

Various embodiments are described below with reference to the drawings wherein.

DETAILED DESCRIPTION OF PREFERRED EMBODIMENT(S)

Figure 1:
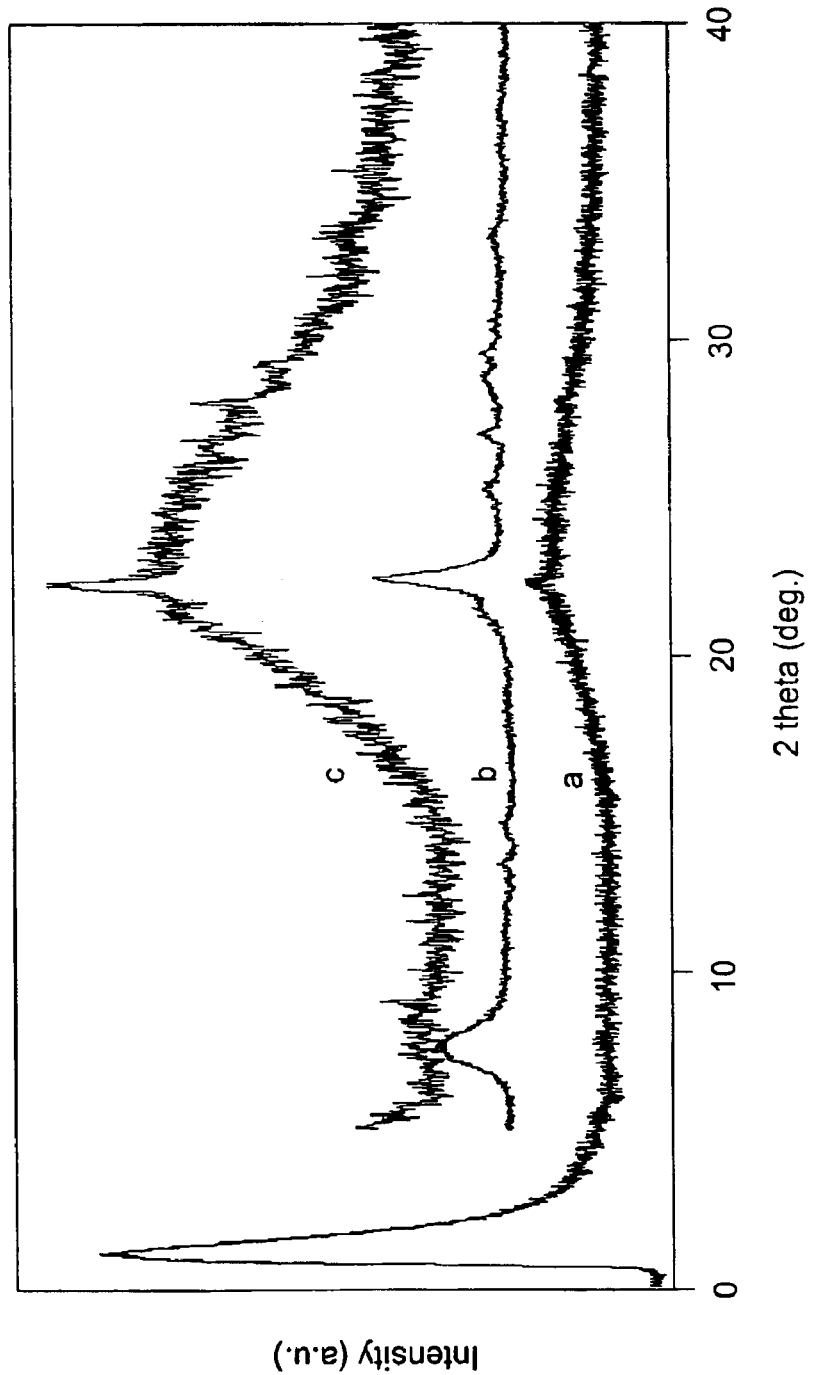
FIG. 1 is a graph showing the X-ray diffraction patterns of pure zeolite beta, mesoporous inorganic oxide support with zeolite beta (Sample 1), and an extended scanning time image of Sample 1.

The catalyst described herein includes a microporous zeolite embedded in a mesoporous support. The microporous zeolite can be any type of microporous zeolite including, but not limited to, zeolite beta, zeolite Y, and ZSM-5. Such zeolites are known in the art and commercially available. The zeolite can be incorporated into the mesoporous support or can be synthesized in-situ in the catalyst support.

The catalyst support is preferably a three dimensional mesoporous inorganic oxide material containing at least 97 volume percent mesopores (i.e., no more than 3 volume percent micropores) based on micropores and mesopores of the organic oxide material (i.e., without any zeolite incorporated therein), and generally at least 98 volume percent mesopores. A method for making a preferred porous silica-containing catalyst support is described in U.S. patent application Ser. No. 09/390,276. The average mesopore size of the preferred catalyst as determined from $N_2$-porosimetry ranges from about 2 nm to about 25 nm. Generally, the mesoporous inorganic oxide is prepared by heating a mixture of (1) a precursor of the inorganic oxide in water, and (2) an organic templating agent that mixes well with the oxide precursor or the oxide species generated from the precursor, and preferably forms hydrogen bonds with it.

The starting material is generally an amorphous material and may be comprised of one or more inorganic oxides such as silicon oxide or aluminum oxide, with or without additional metal oxides. The silicon atoms may be replaced in part by metal atoms such as aluminum, titanium, vanadium, zirconium, gallium, manganese, zinc, chromium, molybdenum, nickel, cobalt and iron and the like. The additional metals may optionally be incorporated into the material prior to initiating the process for producing a structure that contains mesopores. Also, after preparation of the material, cations in the system may optionally be replaced with other ions such as those of an alkali metal (e.g., sodium, potassium, lithium, etc.).

The organic templating agent is preferably a glycol (a compound that includes two or more hydroxyl groups), such as glycerol, diethylene glycol, triethylene glycol, tetraethylene glycol, propylene glycol, and the like, or member(s) of the group consisting of triethanolamine, sulfolane, tetraethylene pentamine and diethylglycol dibenzoate.

The mesoporous catalyst support is a pseudo-crystalline material (i.e., no crystallinity is observed by presently available x-ray diffraction techniques). The wall thickness of the mesopores is preferably from about 3 nm to about 25 nm. The surface area of the catalyst support as determined by BET ($N_2$) preferably ranges from about 400 $m^2/g$ to about 1200 $m^2/g$. The catalyst pore volume preferably ranges from about 0.3 $cm^3/g$ to about 2.2 $cm^3/g$.

The content of zeolite in the catalyst can range from less than about 1% by weight to more than about 99% by weight, preferably from about 5% by weight to 90% by weight, more preferably from about 20% by weight to about 80% by weight. The catalyst with zeolite included preferably contains no more than about 5 volume percent of micropores.

More particularly, the method for making the catalyst includes suspending a zeolite in water. An inorganic oxide precursor is then added to the water and mixed. The inorganic oxide precursor can be a silicate such as tetraethyl orthosilicate (TEOS) or a source of aluminum such as aluminum isopropoxide. TEOS and aluminum isopropoxide are commercially available from known suppliers.

The pH of the solution is preferably kept above 7.0. Optionally, the aqueous solution can contain other metal ions such as those indicated above. After stirring, an organic templating agent which binds to the silica (or other inorganic oxide) species by hydrogen bonding is added and mixed into the aqueous solution. The organic templating agent helps form the mesopores during a pore-forming step, as discussed below. The organic templating agent should not be so hydrophobic so as to form a separate phase in the aqueous solution. The organic templating agent can be one or more compound as listed above. The organic templating agent is preferably added by dropwise addition with stirring to the aqueous inorganic oxide solution. After a period of time (e.g., from about 1 to 2 hours) the mixture forms a thick gel. The mixture is preferably stirred during this period of time to facilitate the mixing of the components. The solution preferably includes an alkanol, which can be added to the mixture and/or formed in-situ by the decomposition of the inorganic oxide precursor. For example, TEOS, upon heating, produces ethanol. Propanol may be produced by the decomposition of aluminum isopropoxide.

The gel is then aged at a temperature of from about 5° C. to about 45° C., preferably at room temperature, to complete the hydrolysis and poly-condensation of the inorganic oxide source. Aging preferably can take place for up to about 48 hours, generally from about 2 hours to 30 hours, more preferably from about 10 hours to 20 hours. After the aging step the gel is heated in air at about 98° C. to 100° C. for a period of time sufficient to dry the gel by driving off water (e.g., from about 6 to about 24 hours). Preferably, the organic templating agent, which helps form the mesopores, should remain in the gel during the drying stage. Accordingly, the preferred organic templating agent has a boiling point of at least about 150° C.

The dried material, which still contains the organic templating agent, is heated to a temperature at which there is a substantial formation of mesopores. The pore-forming step is conducted at a temperature above the boiling point of water and up to about the boiling point of the organic templating agent. Generally, the mesopore formation is carried out at a temperature of from about 100° C. to about 250°, preferably from about 150° to about 200° C. The pore-forming step can optionally be performed hydrothermally in a sealed vessel at autogenous pressure. The size of the mesopores and volume of the mesopores in the final product are influenced by the length and temperature of the hydrothermal step. Generally, increasing the temperature and duration of the treatment increases the percentage of mesopore volume in the final product.

After the pore-forming step the catalyst material is calcined at a temperature of from about 300° C. to about 1000° C., preferably from about 400° C. to about 700° C., more preferably from about 500° C. to about 600° C., and maintained at the calcining temperature for a period of time sufficient to effect calcination of the material. The duration of the calcining step typically ranges from about 2 hours to about 40 hours, preferably 5 hours to 15 hours, depending, in part, upon the calcining temperature.

To prevent hot spots the temperature should be raised gradually. Preferably, the temperature of the catalyst material should be ramped up to the calcining temperature at a rate of from about 0.1° C./min. to about 25° C./min., more preferably from about 0.5° C./min. to about 15° C./min., and most preferably from about 1° C./min. to about 5° C./min.

During calcining the structure of the catalyst material is finally formed while the organic molecules are expelled from the material and decomposed.

The calcination process to remove organic templating agent can be replaced by extraction using organic solvents, e.g., ethanol. In this case the templating agent can be recovered for re-use.

Also, the catalyst powder of the present invention can be admixed with binders such as silica and/or alumina, and then formed into desired shapes (e.g., pellets, rings, etc.) by extrusion or other suitable methods.

Metal ions such as titanium vanadium, zirconium, gallium, manganese, zinc, nickel, iron, cobalt, chromium and molybdenum may be added to the catalyst by impregnation, ion exchange, or by replacing a part of the lattice atoms as described in G. W. Skeels and E. M. Flanigen in M. Occelli, et al., eds., A.C.S. Symposium Series, Vol. 398, Butterworth, pgs. 420–435 (1989).

The catalyst described herein is useful in hydrocarbon processing such as in hydrocracking, hydroisomerization, dewaxing, alkylation, and the like.

For example, alkylation of hydrocarbons with olefins employing catalyst described herein can be performed at a temperature of from about 90° C. to about 250° C., a pressure of from about 10 psig to about 500 psig, and a space velocity of from about 1 WHSV to about 20 WHSV.

Hydrocracking of hydrocarbons employing the catalyst described herein can be performed under reaction conditions including a temperature of from about 200° C. to about 400° C., a pressure of from about 150 psig to about 1,000 psig, and a space velocity of from about 1 WHSV to about 50 WHSV.

Hydroisomerization of hydrocarbons employing the catalyst described herein can be performed under reaction conditions including a temperature of from about 150° C. to about 500° C. a pressure of from about 15 psig to about 3500 psig, and a space velocity of from about 0.1 WHSV to about 20 WHSV.

Catalytic dewaxing of hydrocarbons employing the catalyst described herein can be performed under reaction conditions including a temperature of from about 150° C. to about 500° C., a pressure of from about 100 psig to about 1,500 psig, and a space velocity of from about 0.1 WHSV to about 20 WHSV.

The method of making the catalyst composition of the present invention is illustrated by the Examples 1–5 given below. Example 6 illustrates the use of the catalyst in an alkylation process. Comparative Example A illustrates the use of pure zeolite beta without the mesoporous support described herein and is not in accordance with the present invention. Composition amounts are given in parts by weight.

EXAMPLE 1

First, 1.48 parts calcined zeolite beta with an Si/Al ratio of 24.9 and an average particle size of 1 μm were suspended in 16.32 parts water and stirred for 30 minutes. Then 20.32 parts tetraethylorthosilicate (TEOS) were added to the suspension with stirring. After continuous stirring for another 30 minutes, 9.33 parts triethanolamine were added. After stirring again for another 30 minutes, 4.02 parts tetraethylammonium hydroxide aqueous solution (35% solution available from Aldrich) were added drop-wise to the mixture to increase the pH. After stirring for about 2 hours, the mixture formed a thick non-flowing gel. This gel was aged at room temperature under static conditions for 17 hours. Next, the gel was dried in air at 100° C. for 28 hours. The dried gel was transferred into an autoclave and hydrothermally treated at 170° C. for 17.5 hours. Finally, it was calcined at 600° for 10 hours in air with a ramp rate of 1° C./min.

The final product was designated as Sample 1. The theoretical amount of zeolite beta present in the Sample 1 was 20 wt %. Sample 1 was characterized by X-ray diffraction (XRD), transmission electron microscopy (TEM), nitrogen porosimetry, argon porosimetry and $NH_3$-temperature programmed desorption (TPD). Pure zeolite beta was also characterized by XRD for purposes of comparison.

Referring to FIG. 1, the XRD pattern of the pure zeolite beta, depicted in plot "b", shows the most pronounced characteristic reflections at about 7.7° and 22.2° in 2 theta (33 minute scanning time). The XRD pattern of the mesoporous inorganic oxide support with the zeolite beta crystals (Sample 1) is depicted in plot "a". An intense peak at low angle is observed, indicating that Sample 1 is a mesostructured material. The peaks for beta zeolite are relatively small because the maximum theoretical zeolite content of the final product is only about 20 wt %. When the scanning time for Sample 1 was extended to 45 hours, the characteristic peaks of zeolite beta become clearly visible, as depicted in plot "c".

Figure 2:
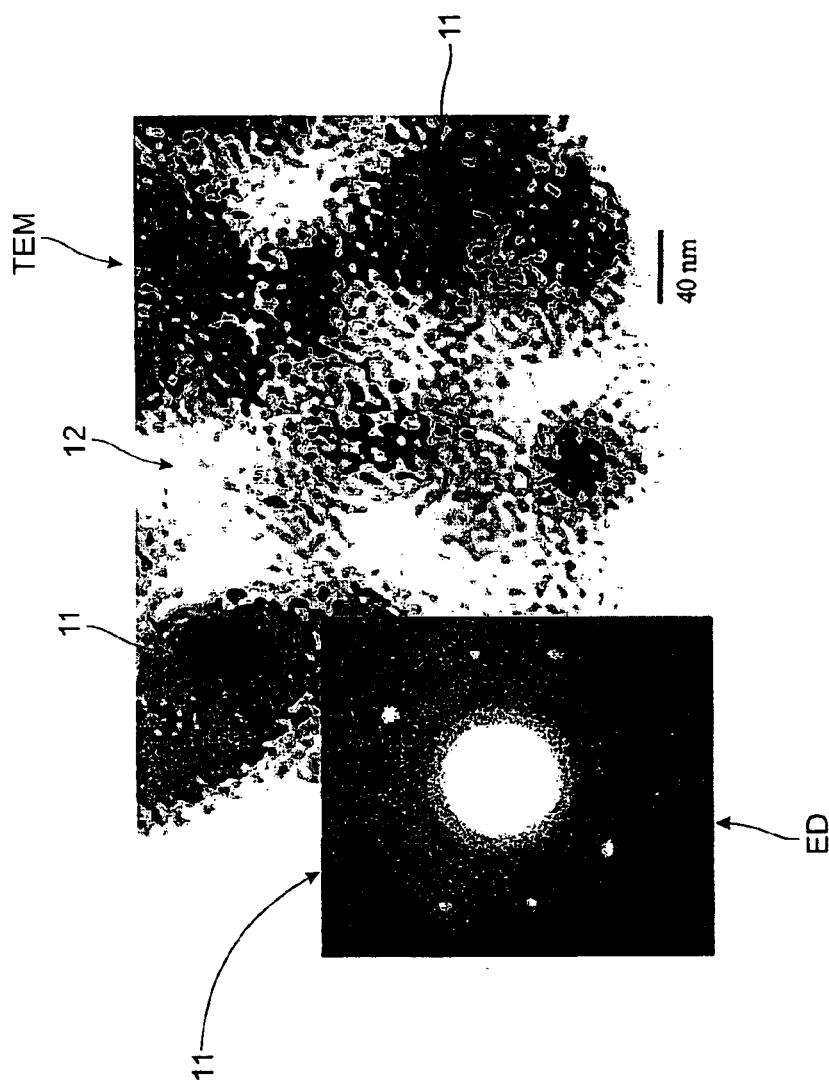
FIG. 2 is a high resolution transmission electron microscopy image of the mesoporous inorganic oxide support with zeolite beta (Sample 1), and an inset showing an electron diffraction pattern of the zeolite domains.

Referring now to FIG. 2, a high resolution transmission electron microscopy image "TEM" of Sample 1 is depicted, which shows dark gray domains 11 in a mesoporous matrix 12. The inset "ED" depicts an electron diffraction pattern which confirms that the dark gray domains 11 are beta zeolite crystals.

Nitrogen adsorption shows that Sample 1 has a narrow mesopore size distribution, mainly centered at about 9.0 nm, high surface area of 710 $m^2/g$ and high total pore volume of 1.01 $cm^3/g$. Argon adsorption shows a peak of micropore size distribution around about 0.64 nm, corresponding to micropore size in zeolite beta. The micropore volume of pores with a diameter smaller than 0.7 nm was 0.04 $cm^3$. This is about 16% of the micropore volume of the pure zeolite beta. Initial addition of uncalcined zeolite beta was 20 wt. % based on the final composite. The used zeolite beta lost about 20 wt. % due to the removal of template during calcination. Taking the mass loss of zeolite during calcination into account, the expected content of zeolite beta in the final composite is about 16 wt. %, which is consistent with the value obtained from micropore volume.

Figure 3:
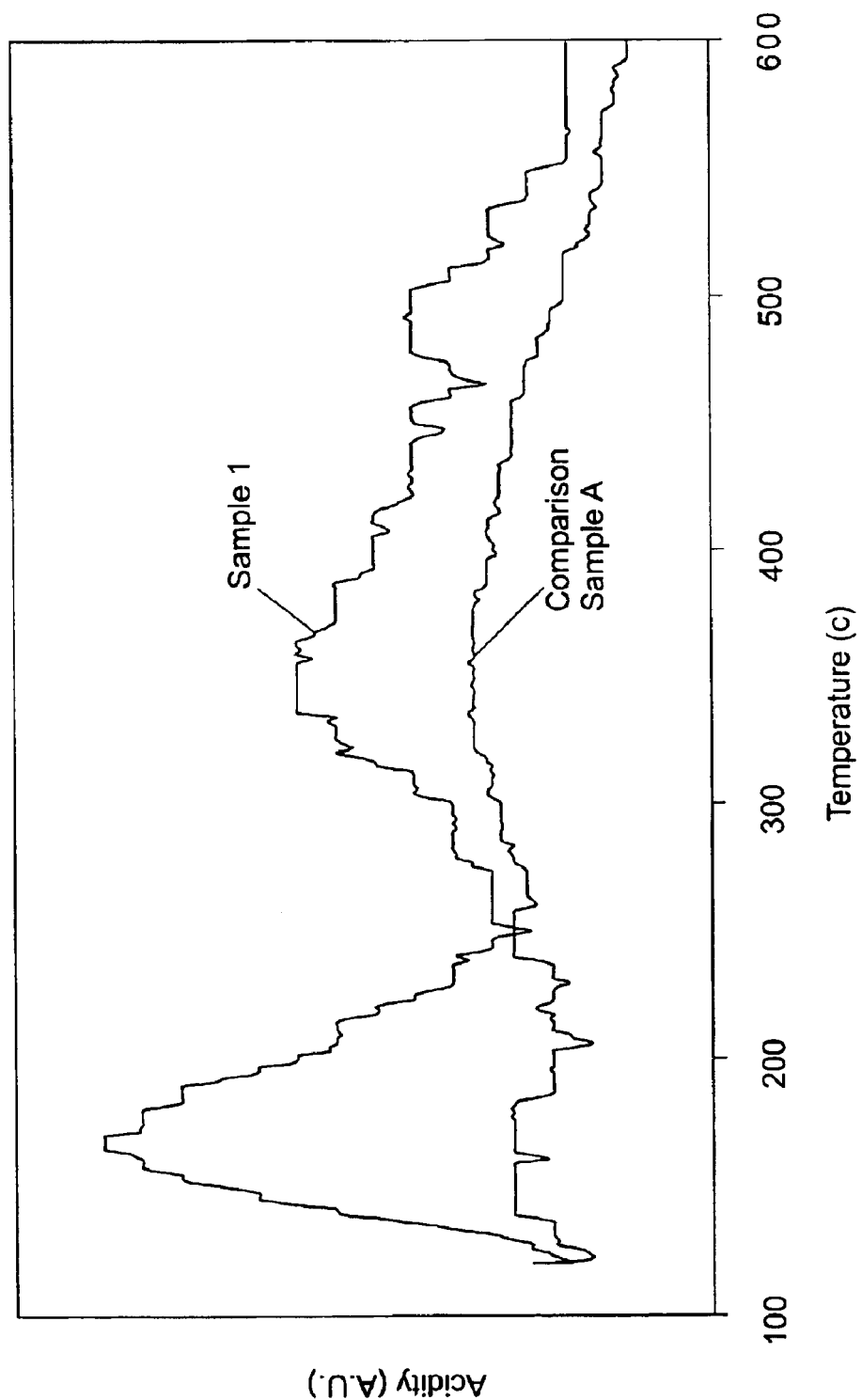
FIG. 3 is a chart showing the temperature programmed desorption of $NH_3$ ($NH_3$-TPD) analysis of the mesoporous inorganic oxide support with zeolite beta (Sample 1), and a comparison sample containing no zeolite beta.

Referring to FIG. 3, the $NH_3$-TPD measurement of Sample 1 showed two desorption peaks, indicating that there are strong acid sites similar to those in zeolites.

EXAMPLE 2

Figure 5:
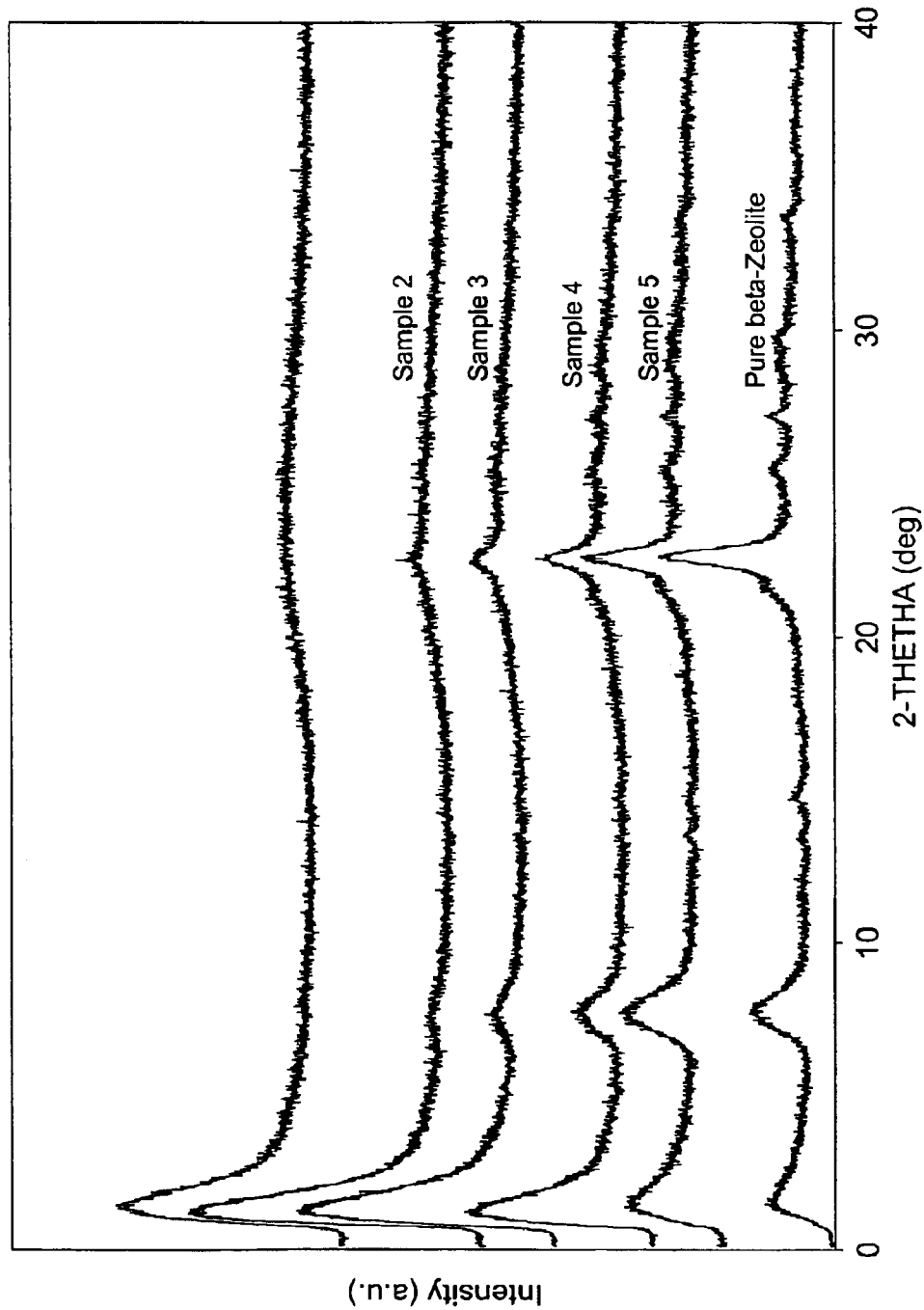
FIG. 5 is a chart showing the X-ray diffraction patterns of the materials produced in Examples 2 to 5 herein, as well as pure zeolite beta.

First, 3.40 parts calcined zeolite beta with an Si/Al ratio of 150 and an average particle size of 0.2 μm were suspended in 84.98 parts water and stirred for 30 minutes. Then 105.80 parts TEOS were added to the suspension with stirring. After continuous stirring for another 30 minutes, 38.27 parts triethanolamine were added. After stirring again for another 30 minutes, 20.93 parts tetraethylammonium hydroxide aqueous solution (35%) were added drop-wise to the mixture. After stirring for about 2 hours the mixture turned into a thick non-flowing gel. This gel was aged at room temperature under static conditions for 24 hours. Next, the gel was dried in air at 98–100° C. for 24 hours. The dried gel was transferred into four 50 ml autoclaves and hydrothermally treated at 180° C. for 4 hours. Finally, it was calcined at 600° C. for 10 hours in air with a ramp rate of 1° C./min. The XRD pattern of the resultant product, designated as Sample 2, is shown in FIG. 5. There is about 10 wt. % zeolite beta in the final composite.

EXAMPLE 3

Figure 4:
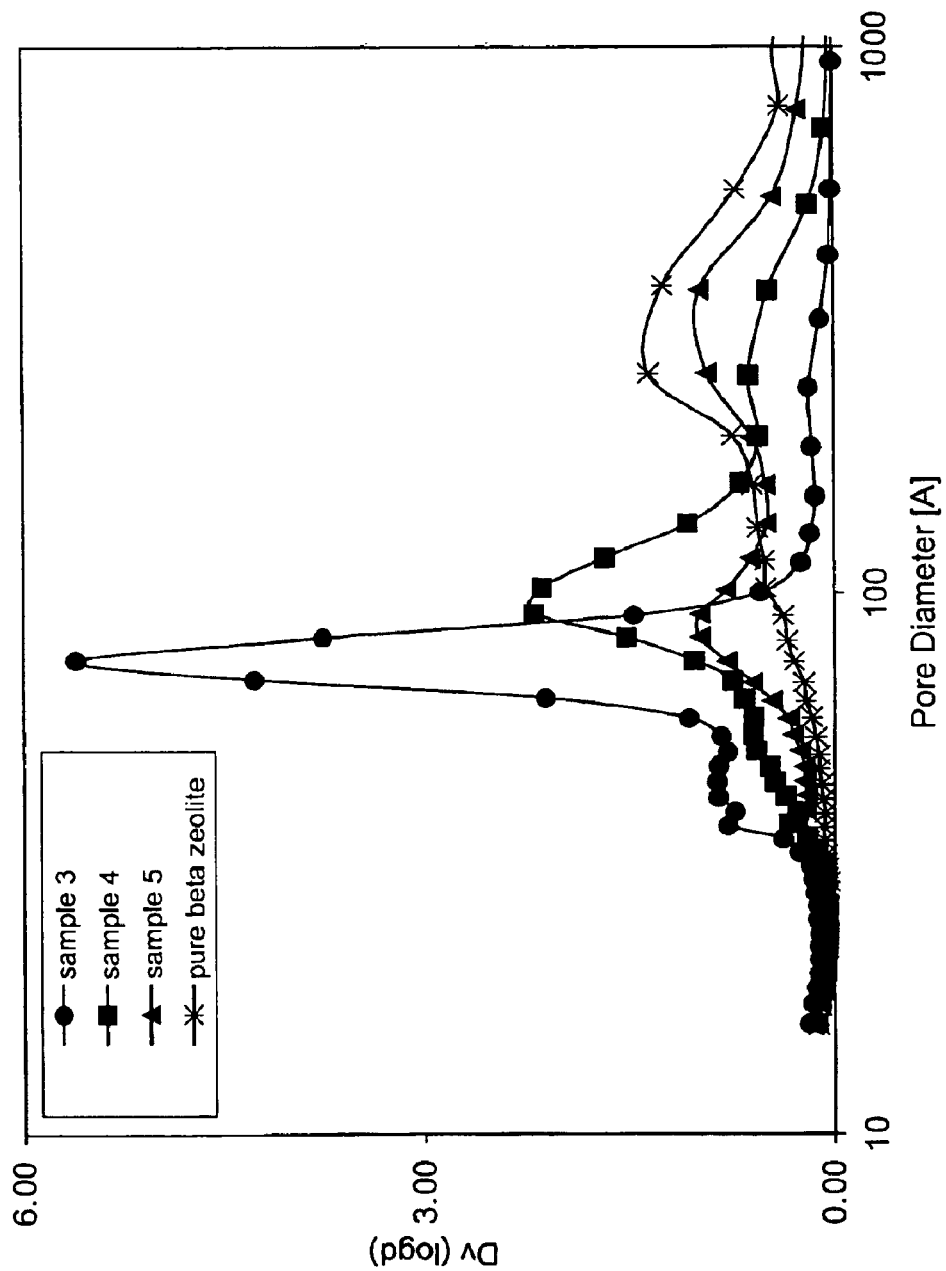
FIG. 4 is a graph showing the mesopore size distribution of the material produced in Examples 3, 4, and 5 herein, and of pure zeolite beta.

First, 4.59 parts calcined zeolite beta with an Si/Al ratio of 150 and an average particle size of 0.2 μm were suspended in 51.02 parts water and stirred for 30 minutes. Then 22.97 parts triethanolamine were added to the suspension with stirring. After continuous stirring for another 30 minutes, 63.50 parts TEOS were added. After stirring again for another 30 minutes, 12.58 parts tetraethylammonium hydroxide aqueous solution (35%) were added drop-wise to the mixture. After stirring for about 2 hours, the mixture formed a thick non-flowing gel. This gel was aged at room temperature under static conditions for 24 hours. Next, the gel was dried in air at 100° C. for 24 hours. The dried gel was transferred into three 50 ml autoclaves and hydrothermally treated at 180° C. for 4 hours. Finally, it was calcined at 600° C. for 10 hours in air with a ramp rate of 1° C./min. The XRD pattern of the resultant product, designated as Sample 3, is shown in FIG. 5, which clearly shows two characteristic peaks of zeolite beta. There is about 20 wt. % zeolite beta in the final composite. Nitrogen adsorption revealed its surface area of about 730 $m^2/g$, pore volume of about 1.08 $cm^3/g$. Its mesopore size distribution is shown in FIG. 4.

EXAMPLE 4

First, 12.23 parts calcined zeolite beta with an Si/Al ratio of 150 and an average particle size of 0.2 μm were suspended in 50.99 parts water and stirred for 30 minutes. Then 22.96 parts triethanolamine were added to the suspension with stirring. After continuous stirring for another 30 minutes, 63.48 parts TEOS were added. After stirring again for another 30 minutes, 12.68 parts tetraethylammonium hydroxide aqueous solution (35%) were added drop-wise to the mixture. After stirring for about 2 hours, the mixture formed a thick non-flowing gel. This gel was aged at room temperature under static conditions for 24 hours. Next, the gel was dried in air at 100° C. for 24 hours. The dried gel was transferred into three 50 ml autoclaves and hydrothermally treated at 180° C. for 4 hours. Finally, it was calcined at 600° C. for 10 hours in air with a ramp rate of 1° C./min. The XRD pattern of the resultant product, designated as Sample 4, is shown in FIG. 5, which clearly shows two characteristic peaks of zeolite beta. There is about 20 wt. % zeolite beta in the final composite. Nitrogen adsorption revealed its surface area of about 637 $m^2/g$, pore volume of about 1.07 $cm^3/g$. Its mesopore size distribution is shown in FIG. 4.

EXAMPLE 5

First, 9.17 parts calcined zeolite beta with an Si/Al ratio of 150 and an average particle size of 0.2 μm were suspended in 16.99 parts water and stirred for 30 minutes. Then 7.65 parts triethanolamine were added to the above suspension under stirring. After continuous stirring for another 30 minutes, 21.16 parts TEOS were added. After stirring again for another 30 minutes, 4.19 parts tetraethylammonium hydroxide aqueous solution (35%) were added drop-wise to the mixture. After stirring for about 2 hours, the mixture formed a thick non-flowing gel. This gel was aged at room temperature under static conditions for 24 hours. Next, the gel was dried in air at 100° C. for 24 hours. The dried gel was transferred into three 50 ml autoclaves and hydrothermally treated at 180° C. for 4 hours. Finally, it was calcined at 600° C. for 10 hours in air with a ramp rate of 1° C./min. The XRD pattern of the resultant product, designated as Sample 5, is shown in FIG. 5, which clearly shows two characteristic peaks of zeolite beta. There is about 60 wt. % zeolite beta in the final composite. Nitrogen adsorption revealed its surface area of about 639 m$^2$/g, pore volume of about 0.97 cm$^3$/g. Its mesopore size distribution is shown in FIG. 4.

EXAMPLE 6

Eight parts of Sample 1 were mixed with two parts of alumina in the form of Nyacol to provide a catalyst. The mixture was dried and calcined by raising the temperature to 120° C. at the rate of 5° C./min, maintaining the 120° C. temperature for one hour, then raising the temperature at the rate of 5° C./min to 500° C. for five hours and finally lowering the temperature at the rate of 5° C./min to 150° C. and then allowing the catalyst to cool to room temperature in a desiccator. The catalyst was then manually crushed and sieved to −12/+20 mesh for activity testing. This catalyst contained 16 wt. % zeolite beta in mesoporous support. A recirculating differential fixed-bed bed reactor was charged with 1.000 gram of catalyst. The recirculating rate (200 gm/min) was about 33 times the feed rate (6.1 gm/min). The loaded reactor was initially filled with benzene, the feed (benzene containing 0.35 wt. % ethylene) was metered in with a metering pump when the reactor reached 190° C. The run was carried out for seven hours. The reaction conditions included a temperature of 190° C. a pressure of 350 psig and a space velocity of 6 WHSV. Feed samples were taken at the beginning, the middle and the end of the run. Product samples were taken every third minute and analyzed by gas chromatography. Based on the rate equation, a rate constant of 0.30 cm$^3$/g-sec was obtained for the alkylation of benzene with ethylene to form ethylbenzene for 16 wt. % zeolite beta-containing catalyst. Alternatively, this value is equivalent of a value of 1.50 cm$^3$/g-sec for a 80 wt. % of zeolite beta-containing catalyst.

COMPARISON SAMPLE A

An all silica mesoporous support was made in accordance with the method described in Example 1 except that no zeolite was incorporated. The resulting support was designated as Comparison Sample A. An NH$_3$-TPD measurement was made of Comparison Sample A and the resulting measurement is depicted in FIG. 3.

COMPARISON EXAMPLE B

A sample of zeolite beta obtained from a commercial supplier and containing 80 wt. % zeolite beta (Si/Al ratio of 4.9) and 20% binder was resized to −12/+20 mesh. The pore size distribution of zeolite beta is depicted in FIG. 4. The activity of the pure zeolite beta of this Comparison Example was tested in the same alkylation reaction using the same methodology and apparatus described in Example 6 above. A rate constant of 0.29 cm$^3$/g-sec was obtained.

Comparing the results of Example 6 with Comparison Example B, the catalyst of Example 6, which is in accordance with the present invention, has about five times greater activity than an equivalent amount of zeolite beta alone for the alkylation of benzene with ethylene. These results indicate that the integrity of the zeolite crystals in the mesoporous catalyst support is maintained during the synthesis of Sample 1. The results also demonstrate that the microporous zeolite beta in the mesoporous support of Sample 1 was still accessible after the synthesis of the catalyst and that the mesopores of the support facilitate mass transfer in aromatic alkylation reactions.

While the above description contains many specifics, these specifics should not be construed as limitations on the scope of the invention, but merely as exemplifications of preferred embodiments thereof. Those skilled in the art will envision many other possibilities within the scope and spirit of the invention as defined by the claims appended hereto.

What is claimed is:

1. A process for treating a hydrocarbon feed comprising:

contacting a feed containing at least one hydrocarbon component with a catalytically effective amount of a catalyst which includes a zeolite supported on a porous noncrystalline inorganic oxide includes micropores and mesopores, wherein an X-ray diffraction pattern of said inorganic oxide includes one peak in 2θ between 0.5 degrees and 2.5degrees, and wherein said mesopores are interconnected mesopores, under conditions sufficient to effect conversions of said hycarbon component.

2. The process of claim 1 wherein the conversion of the hydrocarbon component is effected by means of a hydrocracking reaction, hydroisomerization reaction, dewaxing reaction, or alkylation reaction.

3. The process of claim 1 wherein said feed includes an aromatic compound and an olefin and the reaction conditions are sufficient to effect alkylation of the aromatic compound with the olefin.

4. The process of claim 3 wherein the reaction conditions include a temperature of from about 90° C. to about 250°, a pressure of from about 10 psig to about 500 psig, and a space velocity of from about 1 WHSV to about 20 WHSV.

5. The process of claim 1 wherein the zeolite is a microporous zeolite.

6. The process of claim 5 wherein the microporous zeolite is zeolite beta.

* * * * *